US012673152B2

(12) United States Patent
Li et al.

(10) Patent No.: US 12,673,152 B2
(45) Date of Patent: Jul. 7, 2026

(54) ELECTROOSMOTIC DRIVE MODULE, IMPLANTED ELECTROOSMOTIC MICROPUMP DEVICE, AND AN ELECTRICITY LEADING OUT METHOD

(71) Applicants: HANGZHOU WEIMING XINKE TECHNOLOGY CO., LTD, Hangzhou (CN); ADVANCED INSTITUTE OF INFORMATION TECHNOLOGY (AIIT), PEKING UNIVERSITY, Hangzhou (CN)

(72) Inventors: Liang Li, Hangzhou (CN); Qian Yang, Hangzhou (CN); Meng Gao, Hangzhou (CN); Le Ye, Hangzhou (CN)

(73) Assignees: HANGZHOU WEIMING XINKE TECHNOLOGY CO., LTD, Hangzhou (CN); ADVANCED INSTITUTE OF INFORMATION TECHNOLOGY (AIIT), PEKING UNIVERSITY, Hangzhou (CN)

( * ) Notice: Subject to any disclaimer, the term of this patent is extended or adjusted under 35 U.S.C. 154(b) by 663 days.

(21) Appl. No.: 18/023,876

(22) PCT Filed: Jun. 11, 2021

(86) PCT No.: PCT/CN2021/099625
§ 371 (c)(1),
(2) Date: Feb. 28, 2023

(87) PCT Pub. No.: WO2022/041935
PCT Pub. Date: Mar. 3, 2022

(65) Prior Publication Data
US 2023/0321338 A1     Oct. 12, 2023

(30) Foreign Application Priority Data

Aug. 28, 2020     (CN) ......................... 202010889782.4

(51) Int. Cl.
*A61M 5/142*          (2006.01)

(52) U.S. Cl.
CPC ................................... *A61M 5/142* (2013.01)

(58) Field of Classification Search
CPC ..... A61M 5/142; A61M 31/00; F04B 19/006; F04B 43/06; F04B 19/00; B01D 61/42
See application file for complete search history.

(56) References Cited

U.S. PATENT DOCUMENTS

2016/0258428 A1* 9/2016 Okumura .............. F04B 19/006

FOREIGN PATENT DOCUMENTS

CN          1410673 A      4/2003
CN        106155445 A     11/2016
(Continued)

*Primary Examiner* — Jason E Flick
(74) *Attorney, Agent, or Firm* — MUNCY, GEISSLER, OLDS & LOWE, P.C.

(57)          ABSTRACT

An electroosmotic drive module comprises: a porous dielectric film; two electrodes respectively provided on opposite sides of the porous dielectric film; and a porous insulating layer, one electrode being disposed between the porous dielectric film and the insulating layer. An implantable electroosmotic micropump comprises a housing, and at least one electroosmotic drive module is provided in the housing. There are a plurality of electroosmotic drive modules, and the plurality of electroosmotic drive modules are connected in series end to end, such that heterogeneous integrated assembly between different materials such as electrodes, films, and housings can be achieved.

14 Claims, 9 Drawing Sheets

(56)  References Cited

FOREIGN PATENT DOCUMENTS

| CN | 109790832 | A | | 5/2019 | |
|----|-----------|---|---|--------|---|
| CN | 110898672 | A | | 3/2020 | |
| CN | 112023131 | A | | 12/2020 | |
| CN | 213723893 | U | | 7/2021 | |
| KR | 20170025091 | A | * | 3/2017 | ............. F04B 19/00 |

* cited by examiner

ELECTROOSMOTIC DRIVE MODULE, IMPLANTED ELECTROOSMOTIC MICROPUMP DEVICE, AND AN ELECTRICITY LEADING OUT METHOD

TECHNICAL FIELD

The present disclosure relates to the field of medical device, and specifically to an electroosmotic drive module, an implantable electroosmotic micropump device and an electricity leading out method.

BACKGROUND

An implantable micropump is a device that can be implanted into specific parts inside the human body for targeted drug delivery or fluid drainage. According to the different drive forces of medical micropumps, they can be divided into osmotic pump, vapor pressure pump, spring pressure pump, injection pump, rotor pump, electroosmotic pump, etc. At present, the commercially available implantable micropumps in the market are mainly rotor pumps, and the typical ones include the SynchroMed series of drug infusion pump from Medtronic, Inc., US. However, the rotor pump is of mechanical type, and the mechanical friction movement will cause problems such as heat generation and mechanical power failure, which threaten human health and safety. As compared with the rotor pump, the electroosmotic pump has the advantages of no complicated mechanical structure and friction movement, and is easier to be integrated into a small package of micropump and system; two-way flow rate control is enabled, the operation is simple, and there is very little self-heating, etc. However, there are still some difficulties with the use of electroosmotic pump for long-term implantation. First, the materials selected for the implantable electroosmotic pump have to be biocompatible. The selection of materials for electrode, film, catheter/shell of the electroosmotic pump is limited by the existing implantable biomaterial system. The driving of the electroosmotic pump mainly comes from an electric field generated between the electrodes, and a double electric layer on an inner surface of a porous drive channel. In order to obtain a high flow rate and high pump pressure, under the condition that the structure and materials are determined, increasing an effective voltage difference between the electrodes is a better solution. However, the increase of voltage difference will directly lead to the occurrence of side reactions on electrode surface, such as water electrolysis reaction. Therefore, under the condition of maintaining high pump pressure and high flow rate of the electroosmotic pump, it is a difficult problem to reduce the voltage between electrodes and avoid the occurrence of side reactions on the electrode surface, which is required to be solved particularly. In addition, unlike the rotor pump, the properties of the materials used for the main components (electrodes, porous drive structure and packaging shell) in the electroosmotic pump are quite different. How to realize the small-scale packaging integration of porous dielectric films, electrodes, electrode lead wires and other heterostructures in the electroosmotic micropump device is also a difficult problem required to be solved particularly. Due to the small size of the porous structure of the electroosmotic pump (which is at a micron level, or even nanometer level), the porous structure of the electroosmotic pump will produce a large flow resistance during the sample injection process, which will impede/hinder entry of liquid medicine into a drug delivery catheter through the porous structure during the sample injection process, also bringing great difficulties to the actual operation in the subsequent surgical operation.

SUMMARY

The present disclosure aims to solve the above technical problems in the related art at least to a certain extent. To this end, the present disclosure proposes an electroosmotic drive module, an implantable electroosmotic micropump device and an electricity leading out method.

In order to achieve the above object, a first aspect of the present disclosure provides an electroosmotic drive module, which includes:

a porous dielectric film;

two electrodes, which are arranged on two opposite sides of the porous dielectric film respectively; and a porous insulation layer, one of the electrodes being arranged between the porous dielectric film and the insulation layer.

A second aspect of the present disclosure provides an implantable electroosmotic micropump device, which includes a housing and at least one electroosmotic drive module as described above arranged in the housing, an inner wall of the housing being provided with a liquid filling groove.

A third aspect of the present disclosure provides an assembly method of the electroosmotic drive module, which includes the following steps:

arranging an electrode on one side of the insulation layer, arranging another electrode on one side of the porous dielectric film, and then fixing the side of the insulation layer that is provided with the electrode with a side of the porous dielectric film that is not provided with electrode together; or arranging two electrodes on two opposite sides of the porous dielectric film respectively, and then fixing the insulation layers with the sides of the porous dielectric film that are each provided with the electrode respectively; or arranging two electrodes on two sides of the insulation layers respectively, then fixing the side of one insulation layer that is provided with the electrode with one side of the porous dielectric film, and fixing the side of another insulation layer that is provided with the electrode with the other side of the porous dielectric film.

A fourth aspect of the present disclosure provides an electricity leading out method of the implantable electroosmotic micropump device, which includes the following steps:

arranging electrode conductive wires on the outer wall of the housing, using metal wires to connect the electrode lead-out pins, the conductive wire connecting pins, the electrode lead-out pins or electrodes respectively and welding connection points;

filling the electricity lead-out ports and welding points with a biocompatible material; or patterning the outer wall of the housing by using a mask; and forming the electrode conductive wires on the patterned outer wall of the housing; at the same time, forming a metal connection layer on the electricity lead-out ports, the electrode lead-out pins or the electrodes, and filling the electricity lead-out ports and the metal connection layer with a biocompatible material.

In addition, the above electroosmotic drive module according to the present disclosure may also have the following additional technical features.

According to an embodiment of the present disclosure, a pore size of the insulation layer is larger than that of the porous dielectric film.

According to an embodiment of the present disclosure, a thickness of the insulation layer is larger than the sum of thicknesses of the two electrodes and a thickness of the porous dielectric film.

According to an embodiment of the present disclosure, a pore wall of the insulation layer is provided with an electroosmosis inhibiting coating.

According to an embodiment of the present disclosure, there are a plurality of the electroosmotic drive modules, which are connected in series from head to tail.

According to an embodiment of the present disclosure, an insulation layer is arranged at the electrode at the head or tail.

According to an embodiment of the present disclosure, the implantable electroosmotic micropump device further includes:

two electrode conductive wires, which are arranged on an outer wall of the housing, the housing being provided with electricity lead-out ports, and the electrode conductive wires being electrically connected with the electrodes through the electricity lead-out ports.

According to an embodiment of the present disclosure, the electrodes have electrode lead-out pins, the electrode conductive wires have conductive wire connecting pins, and the electrode lead-out pins pass through the electricity lead-out ports and are connected with the conductive wire connecting pins.

According to an embodiment of the present disclosure, the electrodes are connecting sheets, the electrode conductive wires have conductive wire connecting pins, and the conductive wire connecting pins pass through the electricity lead-out ports and are connected with the electrodes.

According to an embodiment of the present disclosure, the electrode conductive wires are formed on the housing through the process of depositing, sputtering, electroplating or electroless plating.

BRIEF DESCRIPTION OF THE DRAWINGS

Upon reading the detailed description of the preferred embodiments below, various other advantages and benefits will become clear to those skilled in the art. The accompanying drawings are only used for the purpose of illustrating preferred embodiments, and should not be considered as a limitation to the present disclosure. Moreover, throughout the drawings, the same reference signs are used to denote the same components. In the drawings.

DETAILED DESCRIPTION

Figure 1:
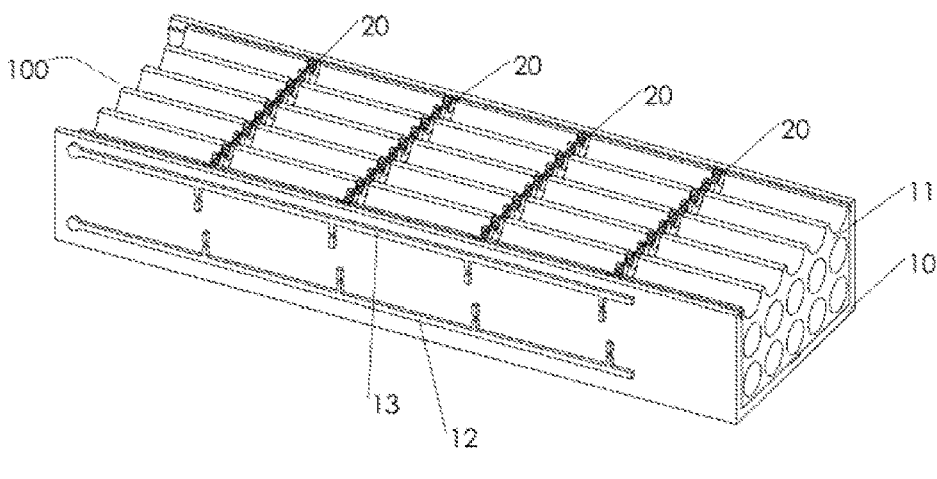
FIG. 1 is a sectional view of an implantable electroosmotic micropump device in some embodiments of the present disclosure.

Hereinafter, exemplary embodiments of the present disclosure will be described in greater detail with reference to the accompanying drawings. Although the exemplary embodiments of the present disclosure are shown in the drawings, it should be understood that the present disclosure may be implemented in various forms and should not be limited by the embodiments set forth herein. On the contrary, these embodiments are provided to enable a more thorough understanding of the present disclosure and to fully convey the scope of the present disclosure to those skilled in the art.

It should be understood that the terms used herein are only for the purpose of describing specific exemplary embodiments, and are not intended to be limitative. Unless clearly indicated otherwise in the context, singular forms "a", "an", and "said" as used herein may also mean that plural forms are included. Terms "include", "comprise" and "have" are inclusive, and therefore indicate the existence of the stated features, elements and/or components, but do not exclude the existence or addition of one or more other features, elements, components, and/or combinations thereof.

In the description of the present disclosure, unless otherwise explicitly specified or defined, terms "arrange" and "connect" should be understood in a broad sense. For example, the connection may be a fixed connection, or a detachable connection, or an integral connection; it may be a direct connection, or an indirect connection implemented through an intermediate medium. For those skilled in the art, the specific meaning of the above terms in the present disclosure can be understood according to specific situations.

In addition, terms "first" and "second" are only used for descriptive purpose, and should not be understood as indicating or implying relative importance or implicitly indicating the number of technical features cited. Therefore, the features defined with "first" and "second" can explicitly or implicitly include one or more of these features. In the description of the present disclosure, "a plurality of" means at least two, such as two, three, etc., unless otherwise defined explicitly and specifically.

For ease of description, spatial relative terms may be used herein to describe the relationship of one element or feature relative to another element or feature as shown in the drawings. These relative terms are, for example, "bottom", "front", "upper", "inclined", "lower", "top", "inner", "horizontal", "outer", etc. These spatial relative terms are intended to include different orientations of a mechanism in use or in operation in addition to the orientation depicted in the drawings. For example, if the mechanism in the figure is turned over, then elements described as "below other elements or features" or "under other elements or features" will be oriented as "above the other elements or features" or "over the other elements or features". Thus, the exemplary term "below" may include orientations of both above and below.

Figure 2:
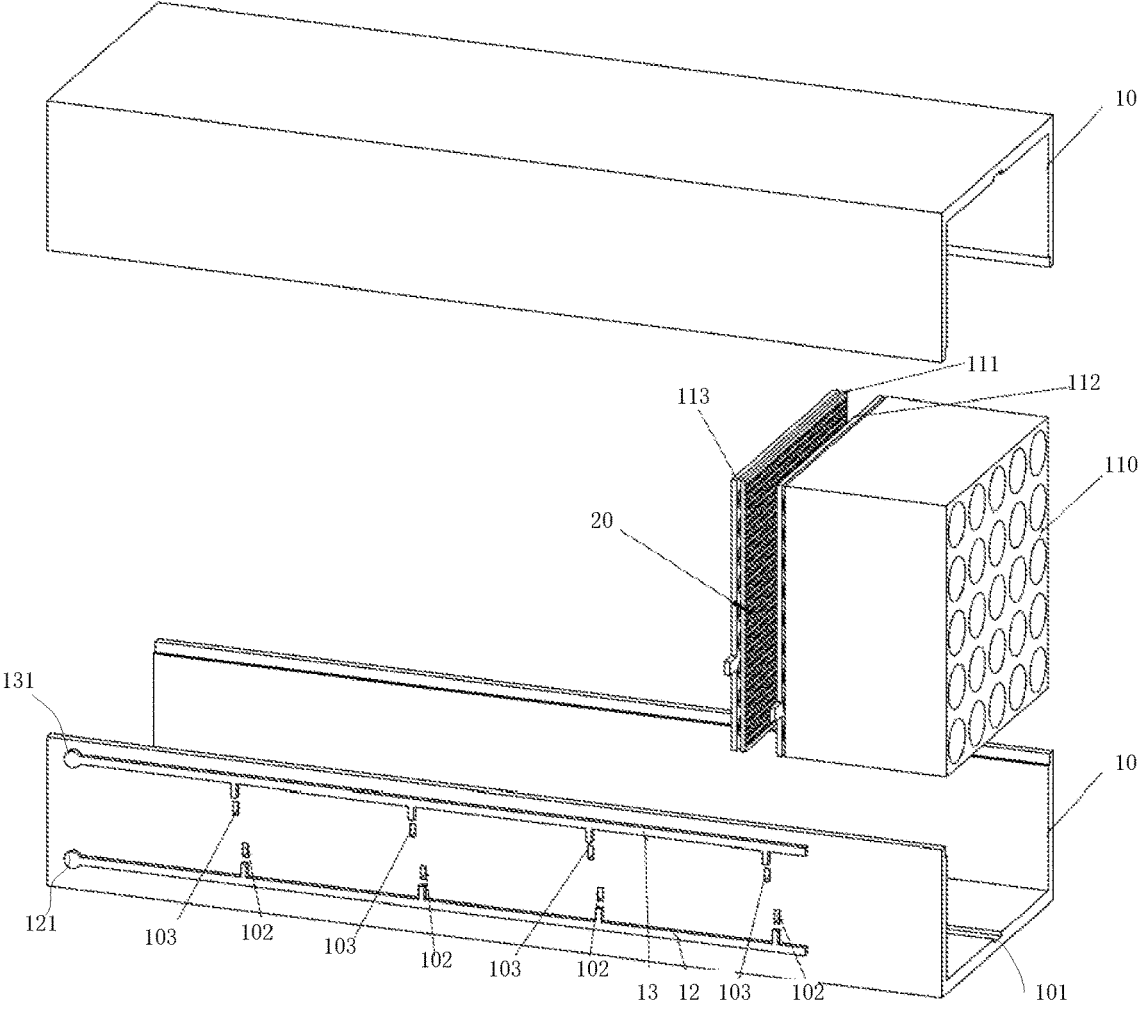
FIG. 2 is a first partially exploded view of FIG. 1.
Figure 3:
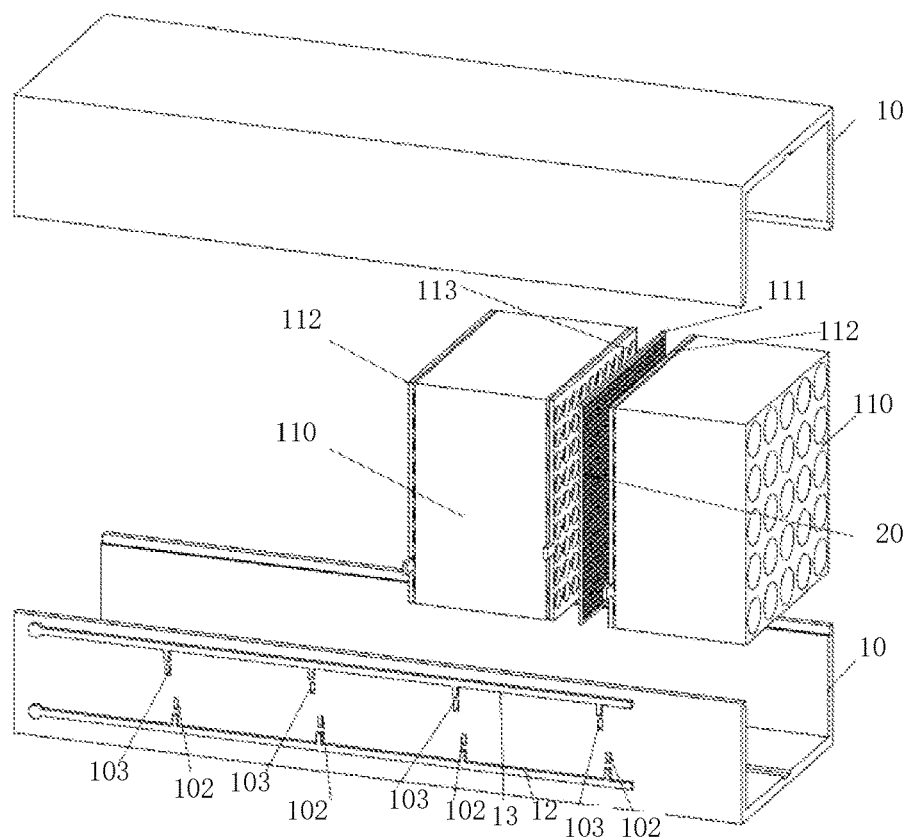
FIG. 3 is a second partially exploded view of FIG. 1.

Referring to FIGS. 1 to 3, some embodiments of the present disclosure provide an implantable electroosmotic micropump device 100, which includes a housing 10, several electroosmotic drive modules 11 arranged in the housing 10, as well as a first electrode conductive wire 12 and a second electrode conductive wire 13 that are arranged on an outer wall of the housing 10. Specifically, this embodiment will be described in an example in which there are four electroosmotic drive modules 11, and the four electroosmotic drive modules 11 connected from head to tail are arranged in the housing 10. Each electroosmotic drive module 11 includes an electroosmotic drive unit 20 and a porous insulation layer 110; the four electroosmotic drive units 20 are connected in series with each other, and the electroosmotic drive unit 20 includes a porous dielectric film 111, a first drive electrode 112 and a second drive electrode 113 that are arranged on two opposite sides of the porous dielectric film 111. The first drive electrode 112 is arranged between the porous dielectric film 111 and the insulation layer 110, the first electrode conductive wire 12 is electrically connected with the first drive electrodes 112, and the second electrode conductive wire 13 is electrically connected with the second drive electrodes 113.

It is worth noting that the insulation layer 110 of each electroosmotic drive module 11 is set as a head of this electroosmotic drive module 11. In this way, the second drive electrode 113 becomes a tail of the electroosmotic drive module 11. A side of the porous dielectric film 111 of a first electroosmotic drive module 11, which is provided with the electrode, is combined and connected in series with a side of the insulation layer 110 of a second electroosmotic drive module 11, which is not provided with electrode, and then a third and fourth electroosmotic drive modules 11 are sequentially connected in series. When the electroosmotic drive modules 11 are connected from head to tail, the second drive electrode 113 on the fourth electroosmotic drive module 11 is necessarily exposed to the outside. At this time, an insulation layer 110 can be arranged at this second drive electrode 113.

Figure 4:
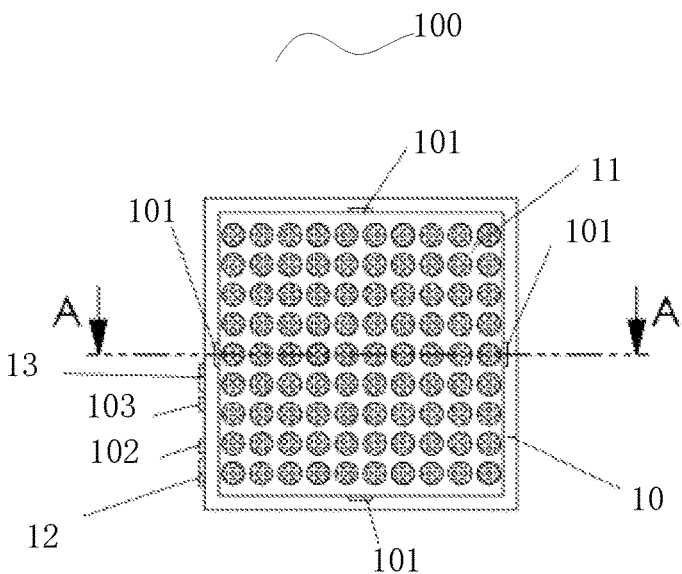
FIG. 4 is a top view of the implantable electroosmotic micropump device in other embodiments of the present disclosure.
Figure 5:
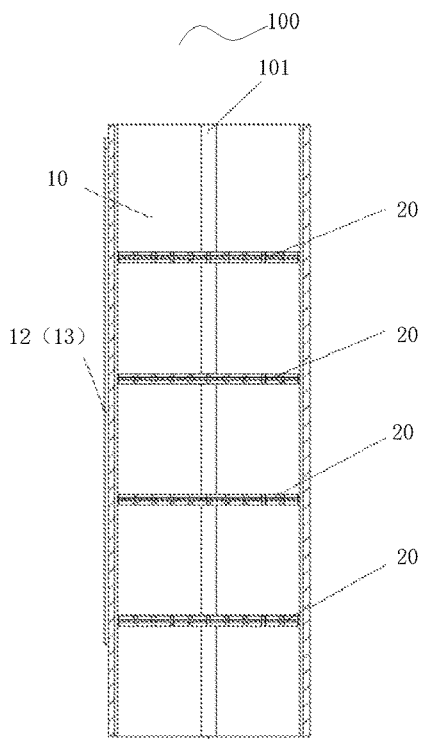
FIG. 5 is a sectional view of FIG. 4 in A-A direction.
Figure 6:
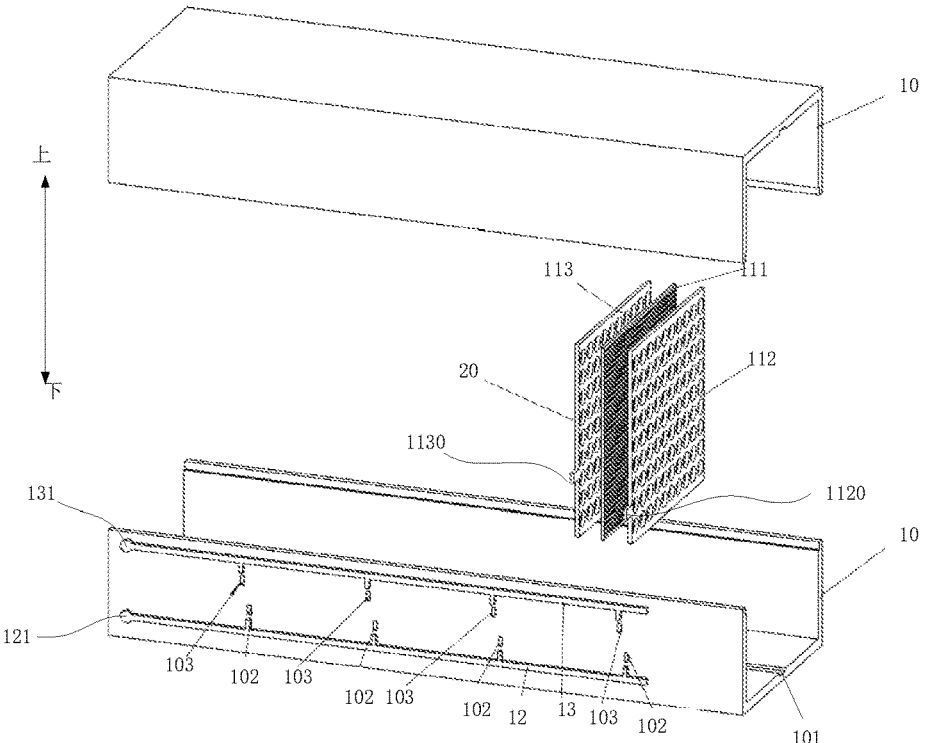
FIG. 6 is a partially exploded view of FIG. 4.

It should be noted that in other embodiments of the present disclosure, as shown in FIGS. 4 to 6, only four electroosmotic drive units 20 connected in series with each other can also be arranged in the housing 10 at intervals, and the spacing between two adjacent electroosmotic drive units 20 is the same. The spacing can be at a millimeter level. The length of the spacing is larger than the thickness of the electroosmotic drive unit 20, and is at least five times the thickness of the porous dielectric film 111.

Specifically, an assembly method of each electroosmotic drive module 11 in this embodiment includes the following steps: fixing or molding the first drive electrode 112 on one side of the insulation layer 110, fixing or molding the second drive electrode 113 on one side of the porous dielectric film 111, and then combining the side of the insulation layer 110 that is provided with the electrode with a side of the porous dielectric film 111 that is not provided with electrode by adhering, bonding and the like to form the electroosmotic drive module 11.

In addition, the assembly method of the electroosmotic drive module 11 may also be carried out through the following steps: for example, arranging two drive electrodes, i.e., the first drive electrodes 112 and the second drive electrode 113, on two opposite sides of the porous dielectric film 111 respectively, and then fixing the insulation layers 110 with the sides of the porous dielectric film 111 that are each provided with the electrode respectively; or arranging two electrodes, i.e., the first drive electrodes 112 and the second drive electrode 113, on two sides of the insulation layers 110 respectively, then fixing the side of one insulation layer 110 that is provided with the electrode with one side of the porous dielectric film 111, and fixing the side of another insulation layer 110 that is provided with the electrode with the other side of the porous dielectric film 111. This embodiment does not limit the assembly method of the electroosmotic drive module 11, and those skilled in the art can choose it flexibly as required. It is worth noting that when four electroosmotic drive modules 11 are assembled in series, they can be assembled through the following method: fixing or molding the first drive electrode 112 and the second drive electrode 113 on two sides of the insulation layer 110 respectively (for the insulation layers of the electroosmotic drive modules 11 at the head and tail, it is only required to fix or mold the drive electrode on one side thereof), and then combining two sides of the porous dielectric film 111 with one insulation layer 110 fixed with the drive electrode(s) respectively through adhering, bonding and the like to complete the assembly of four electroosmotic drive modules 11 in series.

Moreover, in addition to the above assembly method, it is also possible to fix or mold the first drive electrode 112 and the second drive electrode 113 on two opposite sides of the porous dielectric film 111 respectively, and then fix the insulation layers 110 on the sides of the porous dielectric film 111 that are each provided with the electrode respectively. This method can also be used to connect the first drive electrode 112 and the second drive electrode 113 in series.

Specifically, the porous dielectric film 111 can be biocompatible polycarbonate, anodized aluminum oxide, polyurethane, polyethylene terephthalate, poly-p-xylene, porous glass/ceramic, etc., which can be prepared by wet etching, dry etching, mechanical micromachining, laser cutting, injection molding, extrusion, 3D printing, etc. The thickness of the porous dielectric film can be at a micron level, the pore size can be at a nanometer or micron level, and the surface of the pore can be modified by silylation, etc.

Further, the first drive electrode 112 and the second drive electrode 113 can be of ordered porous type, spiral type, or disordered pore structure. It should be noted that the ordered porous type refers to an ordered arrangement of the pores on the first drive electrode 112 and the second drive electrode 113, and correspondingly, the disordered pore structure refers to a disordered arrangement of the pores on the first drive electrode 112 and the second drive electrode 113. Specifically, the first drive electrode 112 and the second drive electrode 113 can be made of metals such as platinum, gold, iridium, titanium, or alloy, porous carbon, conductive polymers (such as PPy, PEDOT, PANI, etc.), or a composite material prepared from the above materials. After being processed into wires, threads, sheets, meshes and other shapes, the first drive electrode 112 and the second drive electrode 113 are respectively bonded and fixed on both sides of the porous dielectric film 111, or they can be directly formed on one or two sides of the insulation layer 110 or the porous dielectric film 111 by means of depositing, sputtering, printing, coating, polymerization and the like. The thickness thereof can be at a micron or submillimeter level, the pore size thereof should be larger than that of the porous dielectric film 111 and can be at a micron or millimeter level.

In some embodiments of the present disclosure, the housing 10 can be prepared from biocompatible materials such as ceramic, glass, silica gel, polyurethane, polytetrafluoroethylene, poly-p-xylene, etc., and four liquid filling grooves 101 are provided on an inner wall of the housing 10. The four liquid filling grooves 101 are arranged around the electroosmotic drive modules 11 to facilitate filling liquid into the implantable electroosmotic micropump device 100. The liquid filling grooves 101 can be square, circular, triangular or trapezoidal grooves, and the size thereof can be at a micron or millimeter level.

In addition, with continued reference to FIG. 6, the housing 10 can be of a split-type, that is, the housing 10 can be divided into an upper half and a lower half After the four electroosmotic drive modules 11 are embedded onto the lower half of the housing 10, the upper half of the housing 10 covers the lower half, and then the upper half and the lower half of the housing 10 are assembled and sealed by plasma bonding, anodic bonding, hot-melt sealing and other methods. It should be noted that the housing 10 can be an integrally formed housing, that is, the housing 10 is formed by integral forming, which is not limited herein by this embodiment.

It is worth noting that the insulation layer 110 has a porous structure, and can be prepared by precision machining, laser cutting, injection molding, extrusion, 3D printing and other methods from polyurethane, polyimide, polymethyl methacrylate, poly-p-xylene, biological silica gel, biological glass, ceramic, etc. The thickness of the insulation layer 110 can be at a millimeter level, is larger than the thickness of the electroosmotic drive unit 20 and at least five times the thickness of the porous dielectric film 111.

When the first drive electrode 112 and the second drive electrode 113 are of the ordered porous structure or disordered pore structure, the pore size of the insulation layer 110 can be at a micron or millimeter level, and is larger than or equal to the pore size of the first drive electrode 112 and the second drive electrode 113. The thickness of the insulation layer 110 also represents the spacing between two adjacent electroosmotic drive units 20, and a pore wall of the insulation layer 110 is treated with an electroosmosis inhibiting coating to form an electroosmosis inhibiting coating on the pore wall of the insulation layer 110, so that there is no electroosmosis or the electroosmosis is very weak on the pore wall of the insulation layer 110.

Figure 7:
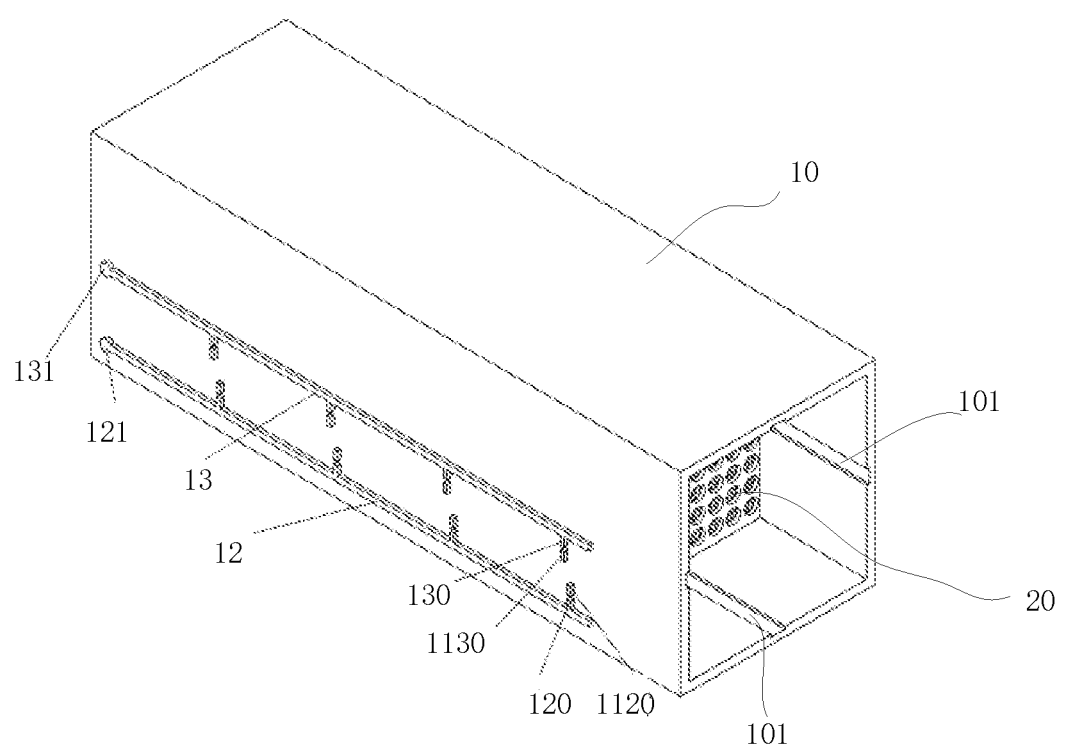
FIG. 7 is a perspective view of FIG. 4.
Figure 8:
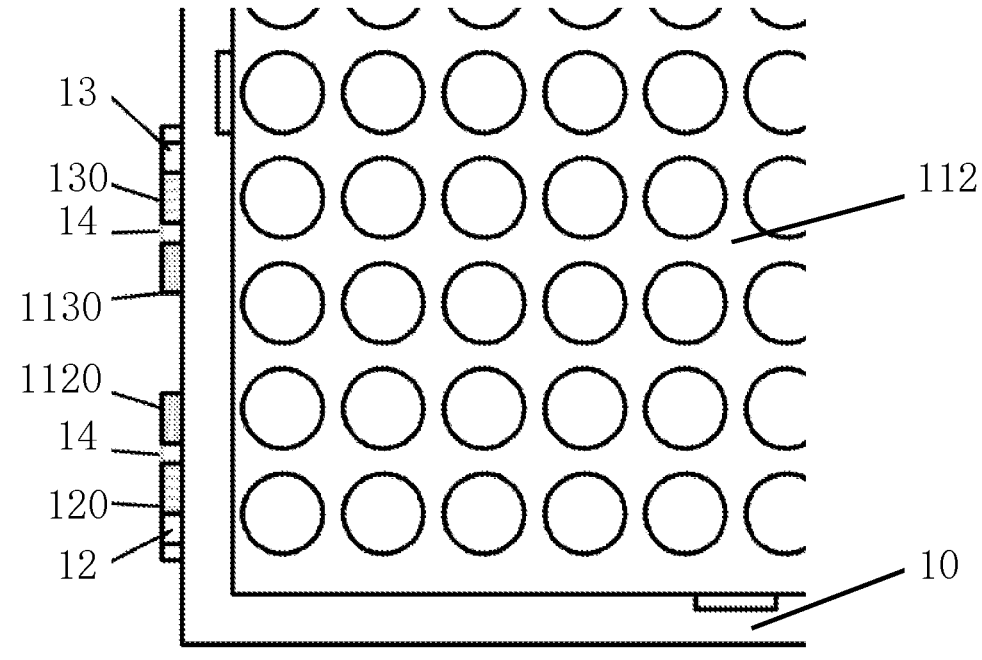
FIG. 8 is a sectional view of an electricity lead-out structure in some embodiments of the present disclosure.

In some embodiments of the present disclosure, as shown in FIGS. 6 to 8, the first drive electrodes 112 and the second drive electrodes 113 are respectively provided with first electrode lead-out pins 1120 and second electrode lead-out pins 1130, and the housing 10 is provided with first electricity lead-out ports 102 and second electricity lead-out ports 103. After the electroosmotic drive modules 11 are assembled into the housing 10, the first electrode lead-out pins 1120 and the second electrode lead-out pins 1130 pass through the first electricity lead-out ports 102 and the second electricity lead-out ports 103 respectively and reach the outside of the housing 10. The first electrode conductive wire 12 and the second electrode conductive wire 13 are formed on the outer wall of the housing 10 by means of depositing, sputtering or printing, or by adhering or bonding metal sheets, threads, wires, etc., and the first electrode conductive wire 12 and the second electrode conductive wire 13 are respectively provided with first conductive wire connecting pins 120 and second conductive wire connecting pins 130. The first conductive wire connecting pins 120 and the second conductive wire connecting pins 130 are electrically connected with the first electrode lead-out pins 1120 and the second electrode lead-out pins 1130. Moreover, one of terminal ends of the first electrode conductive wire 12 and the second electrode conductive wire 13 is respectively provided with a first connection point 121 and a second connection point 131 for connecting with an external circuit.

Specifically, as shown in FIG. 8, the electricity leading out method of the electroosmotic drive module 11 in the housing 10 includes the following steps: selecting metal wires 14 made of gold, platinum, iridium, platinum-iridium alloy, titanium or alloy, etc.; winding one metal wire 14 by N turns (N≥1) on the corresponding first electrode lead-out pins 1120 and first conductive wire connecting pins 120 respectively; winding another metal wire 14 by N turns (N≥1) on the second electrode lead-out pins 1130 and second conductive wire connecting pins 130 respectively; and then spot-welding at the connection points by using the welding process. Finally, biocompatible materials such as poly-p-xylene, epoxy glue and silica gel are coated and filled in the first electricity lead-out ports 102, the second electricity lead-out ports 103 and welding points (not indicated in the drawings), so as to realize the electricity leading out of the drive electrodes, protect the drive electrodes and bonding wires, and reduce the stress.

Figure 9:
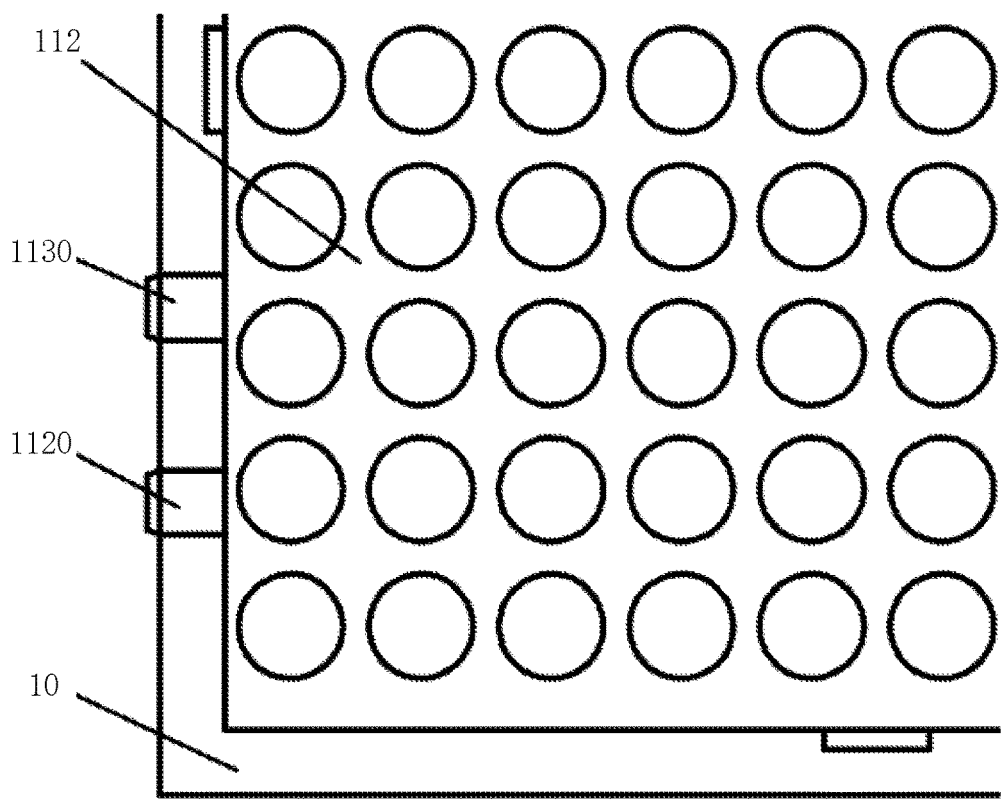
FIG. 9 is a sectional view of electrode lead-out pins in some embodiments of the present disclosure.
Figure 10:
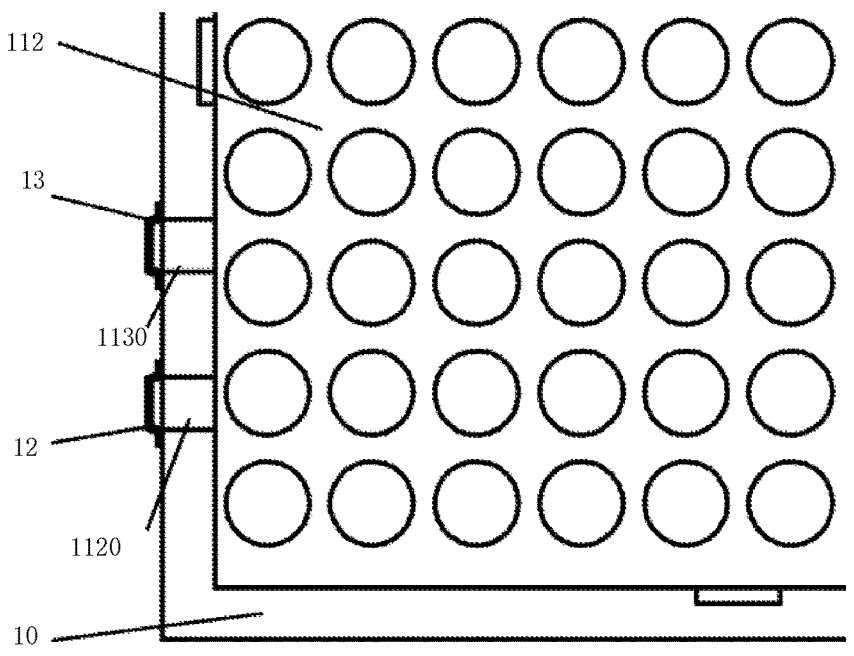
FIG. 10 is a sectional view of FIG. 9 after completion of electricity leading out.

It is worth noting that as shown in FIGS. 9 to 10, one end of the electrode lead-out pin (i.e., the first electrode lead-out pin 1120 and the second electrode lead-out pin 1130) is connected with the drive electrode. In a direction from one end of the electrode lead-out pin to the other end, the end portion of the electrode lead-out pin that extends out of the electricity lead-out port (i.e., the first electricity lead-out port 102 and the second electricity lead-out port 103) has a gradually decreasing cross section, that is, the end portions of the first electrode lead-out pin 1120 and the second electrode lead-out pin 1130 are trapezoidal. In this case, the electricity can also be led out through the following steps: patterning the outer wall of the housing 10 by using a mask; preparing a metal connection layer on the outer side of the housing 10 through the process of depositing or sputtering or electroplating or electroless plating, etc.; at the same time, filling the electricity lead-out ports with a metal connection layer as the first conductive wire connecting pins 120 and the second conductive wire connecting pins 130, and forming the first electrode conductive wire 12 and the second electrode conductive wire 13 on the outer side of the housing 10; after the mask is removed, coating and filling biocompatible materials such as poly-p-xylene, epoxy glue and silica gel in the electricity lead-out ports to protect the drive electrodes and conductive layer and reduce the stress, so that the electricity leading out of the drive electrodes is realized and the electricity is connected to the external circuit through the first connection point 121 and the second connection point 131.

Figure 11:
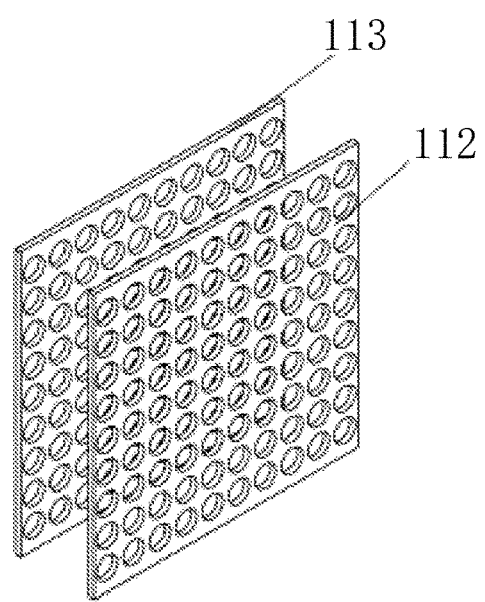
FIG. 11 is a perspective view of drive electrodes without pins in some embodiments of the present disclosure.
Figure 12:
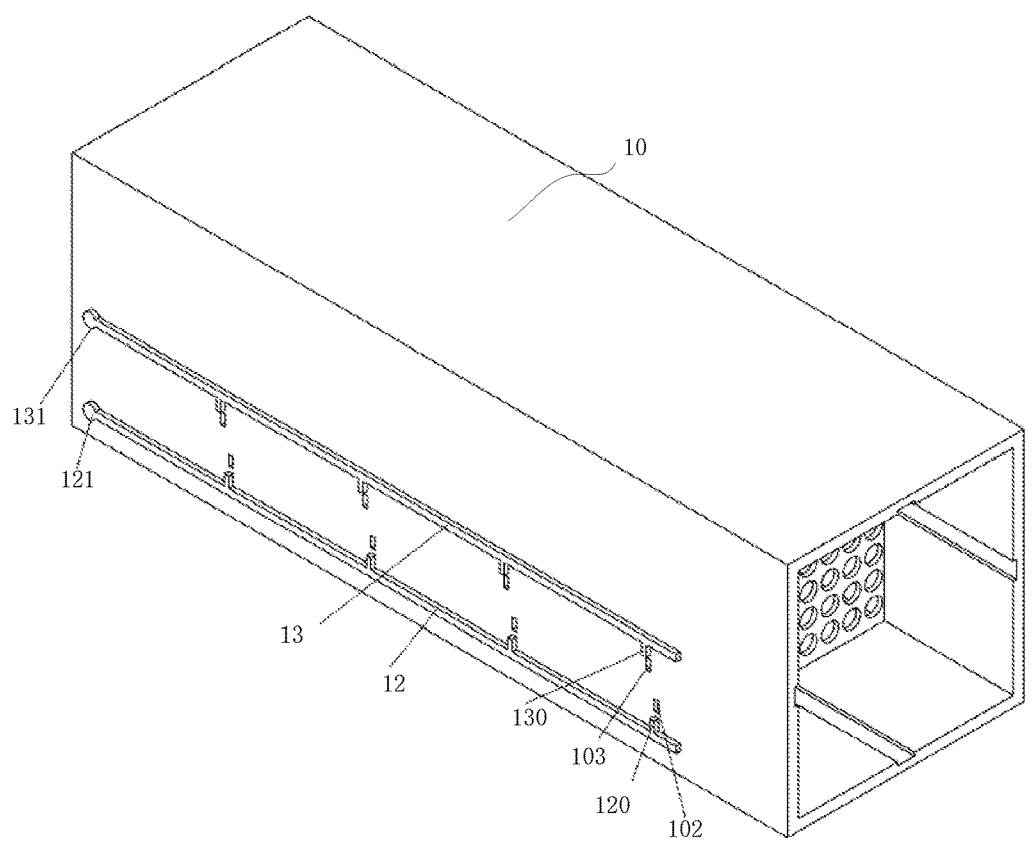
FIG. 12 is a perspective view of FIG. 11 after completion of assembly.
Figure 13:
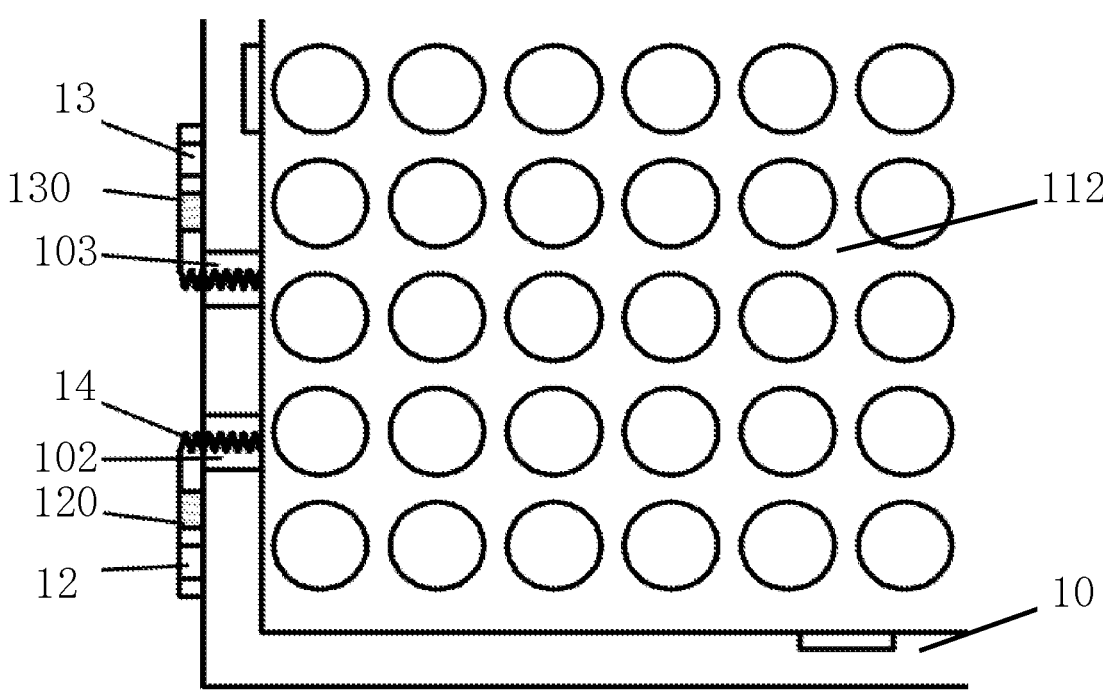
FIG. 13 is a sectional view of a first electricity lead-out structure of the drive electrodes without pins in some embodiments of the present disclosure.

It is worth noting that as shown in FIGS. 11 to 13, when the drive electrode is directly formed on the porous dielectric film 111 or the insulation layer 110 by means of depositing, sputtering, printing, coating, polymerization and the like, the drive electrode has no electrode lead-out pin, that is, the drive electrode is only a connecting sheet. At this time, after the electroosmotic drive module 11 is assembled into the housing 10, the first drive electrode 112 and the second drive electrode 113 cannot reach the outside of the housing 10 directly through the first electricity lead-out port 102 and the second electricity lead-out port 103 on the housing 10. Therefore, in this embodiment, the metal wires 14 extend into the first electricity lead-out port 102 and the second electricity lead-out port 103 respectively to lead out the electricity of the drive electrodes, then the electricity is connected to the first electrode conductive wire 12 and the second electrode conductive wire 13, and connected to the external circuit through the first connection point 121 and the second connection point 131. The specific steps include: selecting two metal wires 14 made of gold, platinum, iridium, platinum-iridium alloy, titanium or alloy, etc., and extending them into the first electricity lead-out port 102 and the second electricity lead-out port 103 respectively; electrically interconnecting the metal wires 14 with the first drive electrode 112 and the second drive electrode 113 respectively by means of wire bonding and the like; spirally winding the metal wires 14 by N turns (N≥1) in the holes of the first electricity lead-out port 102 and the second electricity lead-out port 103; then leading out the metal wires 14 and spirally winding them by N turns (N≥1) on the first conductive wire connecting pin 120 and the second conductive wire connecting pin 130 respectively; and then spot-welding at the connection points by using the welding process. Finally, biocompatible materials such as poly-p-xylene, epoxy glue and silica gel are filled in the first electricity lead-out port 102 and the second electricity lead-out port 103, and glue is filled and coated in the first electricity lead-out port 102, the second electricity lead-out port 103 and welding points (not indicated in the drawings), so as to realize the electricity leading out of the drive electrodes, protect the drive electrodes and bonding wires, and reduce the stress.

Figure 14:
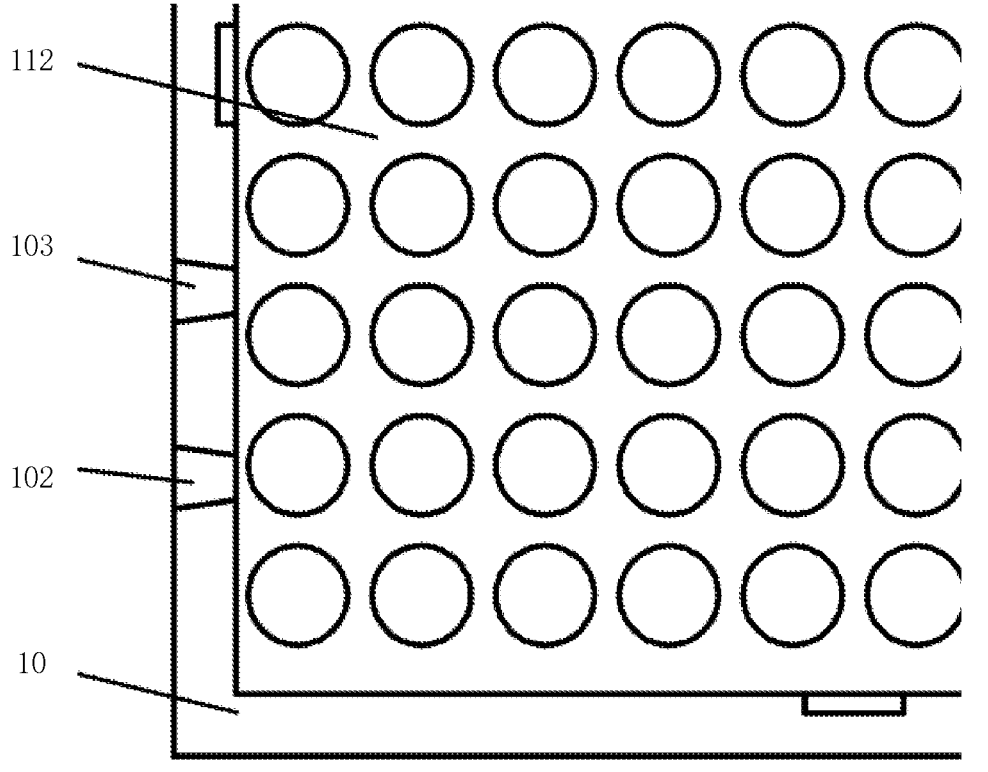
FIG. 14 is a sectional view of electricity lead-out ports of the drive electrodes without pins in some embodiments of the present disclosure.
Figure 15:
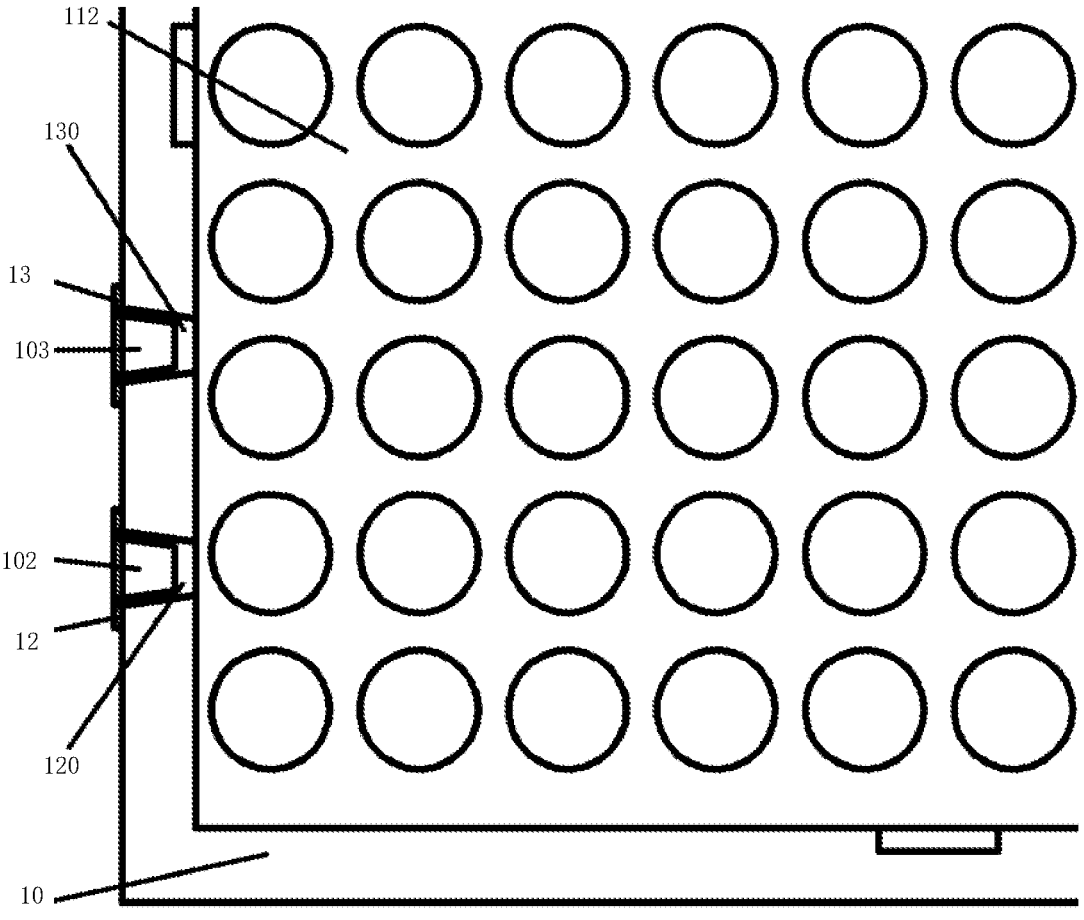
FIG. 15 is a sectional view of the electricity lead-out structure of FIG. 14.
Figure 16:
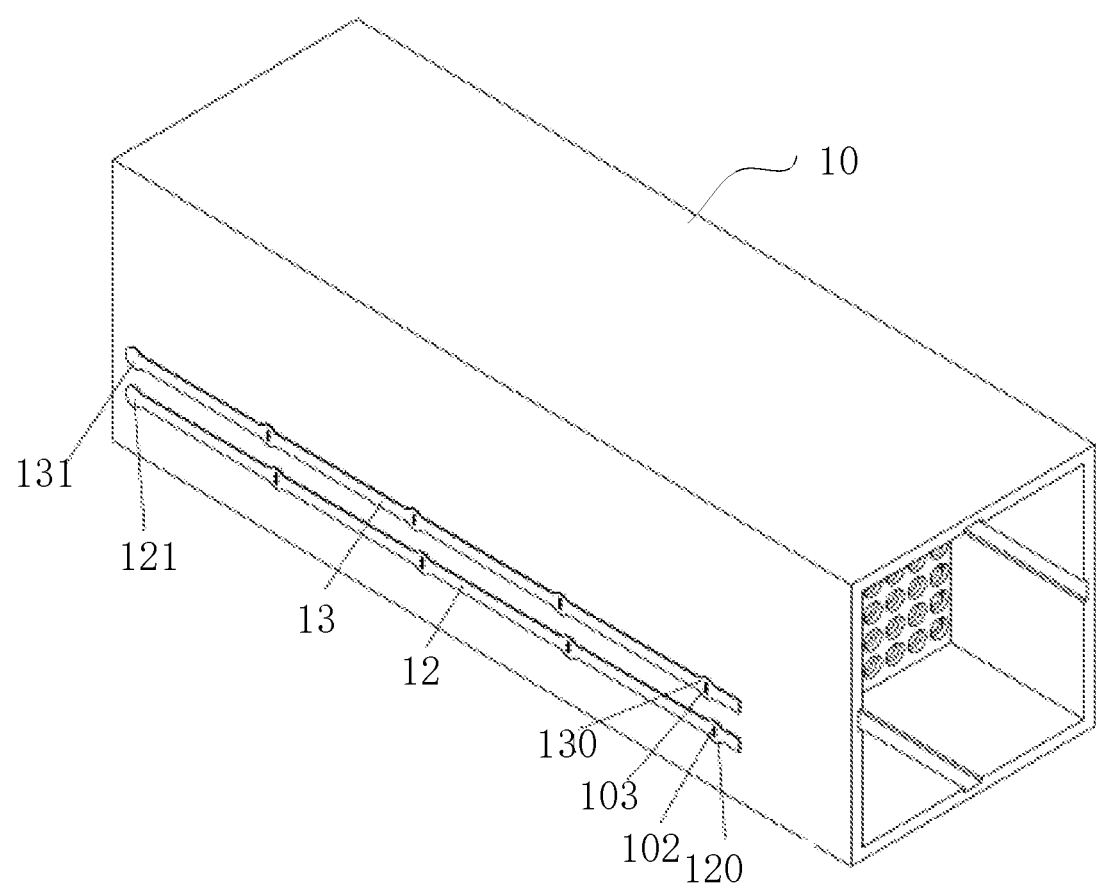
FIG. 16 is a perspective view of the implantable electroosmotic micropump device in some embodiments of the present disclosure.

Further, as shown in FIGS. 14 to 16, in a direction from the inside to the outside of the housing 10, the electricity lead-out port (i.e., the first electricity lead-out port 102, the second electricity lead-out port 103) gradually increases, that is, the electricity lead-out port is trapezoidal, and an opening of the electricity lead-out port on the outside of the housing 10 is larger than an opening of the electricity lead-out port inside the housing 10. In this case, the electricity can also be led out through the following steps: first, preparing a mask with an appropriate shape on the outside of the housing 10; then filling the electricity lead-out ports by means of direct depositing, or sputtering, or electroplating, or electroless plating, etc.; preparing a layer of metal wires on the outer side of the housing 10, that is, forming the first conductive wire connecting pins 120 and the second conductive wire connecting pins 130 in the electricity lead-out ports, and forming the first electrode conductive wire 12 and the second electrode conductive wire 13 on the outer side of the housing 10; after the mask is removed, coating and filling biocompatible materials such as poly-p-xylene, epoxy glue and silica gel in the electricity lead-out ports of the drive electrodes to protect the drive electrodes and conductive layer and reduce the stress, so that the electricity leading out of the drive electrodes is realized and the electricity is connected to the external circuit through the first connection point 121 and the second connection point 131 on the first electrode conductive wire 12 and the second electrode conductive wire 13.

After completing the assembly, integration and electricity leading out of the implantable electroosmotic micropump device, the housing 10 is further wrapped with a layer of packaging shell (not shown in the drawings) made of biocompatible materials such as ceramic, glass, silica gel, polyurethane, polytetrafluoroethylene, and poly-p-xylene.

As compared with the prior art, the implantable electroosmotic micropump device provided by the present disclosure can realize heterogeneous integration and assembly between different materials such as the electrodes, films and housing, so that at the same time of reducing the volume of multiple unit electroosmotic micropump devices, the flow rate and pump pressure of the device under low voltage is improved; by selecting biocompatible materials for fabricating and packaging, the electroosmotic micropump device can be used as an implantable drug delivery pump for targeted drug delivery in human body, and it can also be used as an implantable drainage pump for drainage of accumulated fluid in human body.

Described above are only preferred specific embodiments of the present disclosure, but the scope of protection of the present disclosure is not limited to this. Any change or replacement that can be easily conceived by those skilled in the art within the technical scope disclosed by the present disclosure should be covered within the scope of protection of the present disclosure. Therefore, the scope of protection of the present disclosure shall be accorded with the scope of protection of the claims.

The invention claimed is:

1. An electroosmotic drive module, comprising:
a porous dielectric film;
two electrodes, which are arranged on two opposite sides of the porous dielectric film respectively; and
a porous insulation layer, one of the two electrodes being arranged between the porous dielectric film and the porous insulation layer,
wherein the porous insulation layer has a thickness greater than a thickness of a combination of the two electrodes and the porous dielectric film.

2. The electroosmotic drive module according to claim 1, wherein a pore wall of the porous insulation layer is provided with an electroosmosis inhibiting coating.

3. An implantable electroosmotic micropump device, comprising a housing and at least one electroosmotic drive module according to claim 1 which is arranged in the housing, wherein an inner wall of the housing is provided with a liquid filling groove.

4. The implantable electroosmotic micropump device according to claim 3, wherein there are a plurality of the electroosmotic drive modules, which are connected in series from head to tail, and the porous insulation layer of one of the plurality of the electroosmotic drive modules is arranged at the other one of the two electrodes of another one of a plurality of the electroosmotic drive modules.

5. The implantable electroosmotic micropump device according to claim 4, further comprising:
two electrode conductive wires, which are arranged on an outer wall of the housing, wherein the housing is provided with electricity lead-out ports, and the two electrode conductive wires are electrically connected with the electrodes through the electricity lead-out ports.

6. The implantable electroosmotic micropump device according to claim 5, wherein the electrodes have electrode lead-out pins, the electrode conductive wires have conductive wire connecting pins, and the electrode lead-out pins pass through the electricity lead-out ports and are connected with the conductive wire connecting pins.

7. The implantable electroosmotic micropump device according to claim 5, wherein the electrodes are connecting sheets, the electrode conductive wires have conductive wire connecting pins, and the conductive wire connecting pins pass through the electricity lead-out ports and are connected with the electrodes.

8. An electricity leading out method of the implantable electroosmotic micropump device according to claim 6, comprising the following steps:
arranging the two electrode conductive wires on the outer wall of the housing, connecting the electricity lead-out pins, the conductive wire connecting pins, the electrode lead-out pins or the electrodes respectively by metal wires, and welding connection points of the electrode lead-out pins of the two electrodes, the conductive wire connecting pins of the two electrode conductive wires, the electricity lead-out pins or the two electrodes;

filling the electricity lead-out ports and the connection points with a biocompatible material; or patterning the outer wall of the housing by using a mask; and forming the electrode conductive wires on the patterned outer wall of the housing; simultaneously forming a metal connection layer on the electricity lead-out ports, the electrode lead-out pins or the electrodes, and filling the electricity lead-out ports and the metal connection layer with a biocompatible material.

9. The electricity leading out method of the implantable electroosmotic micropump device according to claim 8, wherein the electrode conductive wires are formed on the housing through a process of depositing, sputtering, electroplating or electroless plating.

10. The electroosmotic drive module according to claim 1, wherein a size of each pore in the porous insulation layer is greater than a size of each pore in the porous dielectric film.

11. The electroosmotic drive module according to claim 1, wherein the thickness of the porous insulating layer is at least five times the thickness of the porous dielectric film.

12. An assembly method of an electroosmotic drive module, comprising the following steps:

arranging a first electrode on one side of a first porous insulation layer, arranging a second electrode on one side of a porous dielectric film, and then fixing the side of the porous insulation layer that is provided with the first electrode with a side of the porous dielectric film that is not provided with second electrode together; or arranging the first and second electrodes on two opposite sides of the porous dielectric film respectively, and then fixing the first porous insulating layer with the side of the porous dielectric film that is provided with the first electrode, and fixing a second porous insulating layer with the side of the porous dielectric film that is provided with the second electrode; or arranging the first electrode on one side of the first porous insulating layer, arranging the second electrode on one side of the second porous insulating layer, then fixing the side of the first porous insulation layer that is provided with the first electrode with a first side of the porous dielectric film, and fixing the side of the second porous insulation layer that is provided with the second electrode with a second side of the porous dielectric film opposite from the first side, wherein each of the first and second porous insulation layers has a thickness greater than a thickness of a combination of the first and second electrodes and the porous dielectric film.

13. The electroosmotic drive module according to claim 12, wherein a size of each pore in the first and second porous insulation layers is greater than a size of each pore in the porous dielectric film.

14. The electroosmotic drive module according to claim 12, wherein the thickness of the first and second porous insulating layers is at least five times the thickness of the porous dielectric film.

* * * * *